United States Patent [19]

DeLuca et al.

[11] 4,035,493
[45] July 12, 1977

[54] RODENTICIDE

[75] Inventors: Hector F. DeLuca; Heinrich K. Schnoes; John W. Suttie; Helen Frank, all of Madison, Wis.

[73] Assignee: Wisconsin Alumni Research Foundation, Madison, Wis.

[21] Appl. No.: 584,900

[22] Filed: June 9, 1975

[51] Int. Cl.$^2$ .......................................... A01N 9/00
[52] U.S. Cl. .............................................. 424/236
[58] Field of Search ................................. 424/236

[56] References Cited

U.S. PATENT DOCUMENTS

| 3,697,559 | 10/1972 | DeLuca et al. | 260/397.2 |
| 3,741,996 | 6/1973 | DeLuca et al. | 260/397.2 |

OTHER PUBLICATIONS

Burhl et al., Chem. Abst., vol. 49, 9772 (1955).

Primary Examiner—Allen J. Robinson
Attorney, Agent, or Firm—Howard W. Bremer

[57] ABSTRACT

A rodenticide suitable for the control of rat and mice populations containing as the active rodenticidal ingredient 1α-hydroxycholecalciferol or 1α-hydroxyergocalciferol or 1,25-dihydroxycholecalciferol.

6 Claims, No Drawings

RODENTICIDE

The invention described herein was made in the course of work under a grant or award from the Department of Health, Education, and Welfare.

This invention relates to rodenticides and food baits containing them.

More specifically, this invention relates to rodenticides which are eminently effective against mice and anticoagulant rodenticide resistant rats as well as normal rats.

Still more specifically this invention relates to rodenticides and rodenticide food baits wherein the essential rodenticide ingredient is selected from the group consisting of 1α-hydroxycholecalciferol, 1α-hydroxyergocalciferol and 1,25-dihydroxycholecalciferol.

At one time or another many rodenticidal agents have been suggested and used in an effort to control rodent populations. The quick-acting single-dose stomach poisons were for many years the rodenticides of choice but their successful use was attended by many problems. Among these was the "bait-shyness" developed by the rodents which adversely affected intake of the rodenticide and the inherent danger in the use of such poisons where accessibility to other animals, or secondary poisoning effects from the consumption of poisoned rodents, was a distinct possibility. In more recent years the quick-acting, single-dose stomach poisons have been largely supplanted by the multiple-dose anticoagulant rodenticides because of their efficacy and relative safety. Examples of such rodenticides are certain indandione derivatives such as, for example, 2-pivalyl-1,3-indandione, and the 3-substituted-4-hydroxycoumarins, most notable of which is warfarin.

It is now well known that strains of wild rats exist which are resistant to the action of anticoagulant rodenticides and that rat populations exhibiting this trait are being increasingly found. This, of course, presents a serious problem and makes present rodent control less efficacious than is desirable. Moreover, it is also recognized that the anticoagulant rodenticides are not highly effective against mice.

It has now been found that rodents, including normal rats, anticoagulant-rodenticide resistant rats and mice, can be effectively controlled through the use of 1α-hydroxycholecalciferol or 1α-hydroxyergocalciferol or 1,25-dihydroxycholecalciferol as the active rodenticide.

1α-hydroxycholecalciferol (hereinafter 1α-HCC), 1α-hydroxyergocalciferol (hereinafter 1α-HEC) and 1,25-dihydroxycholecalciferol (hereinafter 1,25-DHCC) are all compounds closely related in structure to the D vitamins. (See for example U.S. Pat. No. 3,741,996, 3,697,559 and "1α-Hydroxyvitamin $D_2$: A Potent Synthetic Analogue of Vitamin $D_2$", H. Y. Lam, H. K. Schnoes, H. F. DeLuca, Science, Vol. 186, pp. 1038–1040, 1974.)

It has been suggested that vitamin $D_2$ itself might be an effective rodenticide and tests have been conducted with baits containing 0.1 percent calciferol and showing reasonable effectiveness. (See Anticoagulant Resistance Studies Quarterly Report, Jan. 1. 1975 through Mar. 31, 1975 of the Rodent Control Evaluation Laboratory, Troy, N.Y. of the New York State Department of Health, Bureau of Rodent Control.) There are however a number of disadvantages attendent upon such use of calciferol or, alternatively, cholecalciferol (vitamin $D_3$). The levels of use must be substantial as compared with the rodenticides of the present invention — 10 to 20 mg of vitamin $D_3$ being required to kill about a 150 gram rat while with 1α-HCC 100–200 μg will kill. Also, based upon relative activities, 1α-HEC will function for rodenticidal purposes at the same level as 1α-HCC and with 1,25-DHCC about 500 μg will suffice to kill the same size rat. Thus, it is apparent that 1α-HCC is about 1000 times more effective as a rodenticide than vitamin $D_3$. This, of course, also means that the rodenticides of the present invention will be considerably cheaper for the same degree of effectiveness.

In addition to the foregoing advantage the rodenticides of the present invention appear to be tasteless to the rodent and hence will not engender "bait-shyness" in the animals. Furthermore, metabolic studies indicate that 1α-HCC and 1α-HEC will be metabolized quite rapidly within the animal body — usually within 48 hours after a small dose — to known metabolic forms of vitamin D. Thus, rodents ingesting the rodenticides of this invention will not retain these materials in their bodies in unaltered form and should therefore present no secondary poisoning danger to those animals consuming such rodents. This is, of course, in contrast with the use of calciferol or cholecalciferol, where ingestion of much larger quantities are required for kill, and where retention of the ingested material in unaltered form in the rodent can present a real secondary poisoning hazard.

Although there is no intention to be bound by theoretical considerations, it is believed that the rodenticides of this invention function by superstimulating calcification mechanism in the rodent and are then degraded within the rodent body while calcification continues at a high rate. This is believed supported by the observations from autopsies of animals killed with such rodenticides where death appeared to result primarily from nephrocalcinosis and from clacification of heart and aortic tissue. Also, it is believed that effectiveness of the rodenticides of this invention are attributable to the presence of a hydroxyl substituent at the 1-position in the molecule.

By way of illustrating the present invention 1α-HCC was used as the rodenticide in the following Examples.

In the Examples, the 150 gram albino rats were obtained from the Holtzman Company of Madison, Wisconsin, the warfarin-resistant (anticoagulant-rodenticide resistant) were obtained from a colony maintained by Professor John W. Suttie at the University of Wisconsin-Madison and the mice were obtained from Jackson Laboratories, Bar Harbor, Me.

In all cases the animals were placed in overhanging wire cages and fed the standard Environmental Protection Agency rodenticide test diet consisting of 65% coarse ground corn, 25% ground oats, 5% powdered sugar and 5% corn oil to which had been added the 1α-HCC dissolved in Wesson Oil (a commercially available product comprising cottonseed oil and soybean oil in admixture and sold by Wesson-Hunt Foods) so that the diet contained 20 mg of 1α-HCC per kilogram of diet (200 μg 1α-HCC/10 gms. diet). The animals were given access to the 1α-HCC-containing diet and to water ad libitum. Diet consumption was recorded daily and the animals observed periodically.

The results obtained are shown below.

Example 1

| Animal Identity | Amount of Diet Consumed | Number of Days Until Death |
|---|---|---|
| 6 Warfarin-resistant Rats<br>Average weight - 230 g | 15 grams/rat | 6/6 – 4 days |

The effectiveness of 1α-HCC against warfarin-resistant rats is readily evident for the foregoing data.

Example 2

| Animal Identity | Amount of Diet Consumed | Number of Days Until Death |
|---|---|---|
| 6 Albino (Holtzman) Rats<br>Average weight - 150 g | 10 grams/rat | 6/6 – 5 days |

Example 3

| Animal Identity | Amount of Diet Consumed | Number of Days Until Death |
|---|---|---|
| 6 Mice<br>Average weight | 5 grams/mouse | 5/6 – 6 days<br>6/6 – 7 days |

The effectiveness of 1α-HCC against mice is readily evident from the above table.

The substitution of 1α-HEC for 1α-HCC in the preceding Examples will give comparable results and the use of 1,25-DHCC in lieu of 1α-HCC will show highly acceptable rodenticidal activity with all of the rodenticides of this invention exhibiting a much smaller range between effectiveness and toxicity than vitamin $D_3$, evidentiary of unexpectedly high toxicity in the rat. It is also to be understood that since 1α-HCC, 1α-HEC and 1,25-DHCC exhibit a high toxicity in other than rodent species their application as pesticides for undesirable avian and other species will be apparent.

Having thus described the invention what is claimed is:

1. A method for controlling rat and mice populations which comprises making available to such populations a rodenticidally effective amount of a rodenticidal compound selected from the group consisting of 1α-hydroxycholecalciferol, 1α-hydroxyergocalciferol and 1,25-dihydroxycholecalciferol.

2. The method of claim 1 wherein the rat population contains anticoagulant arodenticide-resistant rats.

3. The method of claim 1 wherein the rodenticidal compound is 1α-hydroxycholecalciferol.

4. A method for controlling rat and mice populations which comprises making available to such populations, in amounts sufficient to effect control, a rodenticide food bait comprising edible material acceptable to rodents and, as the essential rodenticidal ingredient, a compound selected from the group consisting of 1α-hydroxycholecalciferol, 1α-hydroxyergocalciferol and 1,25-dihydroxycholecalciferol.

5. The method of claim 4 wherein the rodenticidal food bait contains, as the essential active rodenticidal ingredient, 1α-hydroxycholecalciferol.

6. The method of claim 5 wherein the 1α-hydroxycholecalciferol is present in an amount of about 20 μg/gram of bait.

* * * * *